United States Patent [19]

King et al.

[11] Patent Number: 4,626,542
[45] Date of Patent: Dec. 2, 1986

[54] 4-(5H-DIBENZO[A,D]CYCLOHEPTEN-5-YL)PIPERIDINE COMPOUNDS, PHARMACEUTICAL COMPOSITIONS AND METHODS

[75] Inventors: Stella W. King, Lansdale; David C. Remy, North Wales, both of Pa.

[73] Assignee: Merck & Co., Inc., Rahway, N.J.

[21] Appl. No.: 596,955

[22] Filed: Apr. 5, 1984

[51] Int. Cl.$^4$ .......................................... A61K 31/445
[52] U.S. Cl. .................................... 514/325; 546/203
[58] Field of Search ........................ 546/203; 514/325

[56] References Cited

U.S. PATENT DOCUMENTS 2,985,660  5/1961  Judd et al. ........................... 546/203
3,014,911  12/1961  Engelhardt ........................... 546/203
4,022,902  5/1977  Remy ............................... 546/203 X
4,355,036  10/1982  Villani ............................. 546/203 X

OTHER PUBLICATIONS

Fieser et al., Reagents for Organic Synthesis, (1979), pp. 387–388; John Wiley and Sons.
Engelhardt et al., J. Med. Chem., 8, pp. 829–835 (1965).
Merck Index, vol. 10, pp. 398–399 (1983).
Lowe et al., Br. J. Pharmac., 74, pp. 651–663 (1981).

Primary Examiner—Joseph Paul Brust
Attorney, Agent, or Firm—Salvatore C. Mitri; Michael C. Sudol

[57] ABSTRACT

Pharmaceutical compositions comprising 4-(5H-dibenzo[a,d]cyclohepten-5-yl)piperidine compounds and the use of 4-(5H-dibenzo[a,d]cyclohepten-5-yl)piperidine compounds for treatment of certain cardiovascular disorders are disclosed.

1 Claim, No Drawings

4-(5H-DIBENZO[A,D]CYCLOHEPTEN-5-YL)PIPERIDINE COMPOUNDS, PHARMACEUTICAL COMPOSITIONS AND METHODS

The present invention is directed to compositions comprising 4-(5H-dibenzo[a,d]cyclohepten-5-yl)piperidine compounds and the use of said compounds in the treatment of certain cardiovascular disorders.

BACKGROUND OF THE INVENTION

It is known that calcium ions (Ca++) play vital roles in many cell processes. Calcium ions are particularly important to the function of cardiac tissue and vascular smooth muscle. The transition from the resting to the active state in the myocardium is initiated by cell depolarization which may be recorded as transmembrane action potential comprising a sharp peak caused by movement of sodium ions into the cell followed by a prolonged plateau during which calcium ions move into the cell. When intracellular concentration of calcium ions rises above about $10^{-7}M$,, contraction occurs. The elevation of Ca++ concentration is believed to remove the inhibitory influence of the troponintropomyosin complex on the actin and myosin necessary for contraction.

The movement of sodium and calcium ions into the cells is considered to be through "channels" in the cell membrane. The extent of influx of Ca++ appears to be dependent on the number of channels open and the extent of their opening. The extent of opening appears to be dependent on membrane depolarization, phosphorylation of certain protein kinases, and activation of specific membrane receptors. The channels may be blocked by certain chemical compounds.

In view of the central role played by Ca++ in the electrophysiological and mechanical properties of the heart, and in the systemic and coronary arteries, the blocking of Ca++ channels can produce alterations in cardiovascular functions which can be advantageously employed in the treatment of a wide variety of cardiac disorders including cardiac arrhythmias, angina pectoris, arterial hypertension, hypertrophic obstructive cardiomyopathy and the like.

The effect of chemical compounds on the role played by Ca++ in cardiovascular functions is still being studied and suitable drugs are still being sought. Compounds which have been reported to be active as calcium entry blockers (sometimes referred to as calcium channel blockers) represent different types of chemical compounds. Thus, some of drug names and their chemical names are as follows: Nifedipine, 1,4-dihydro-2,6-dimethyl-4-(2-nitrophenyl)-3,5-pyridinedicarboxylic acid dimethyl ester; Verapamil, α-[3-[[2-(3,4-dimethoxyphenyl)ethyl]methylamino]propyl]-3,4-dimethoxy-α-(1-methylethyl)benzeneacetonitrile; Prenylamine, N-(1-methyl-2-phenylethyl)-α-phenylbenzenepropanamine; Perhexiline, 2-(2,2-di-cyclohexylethyl)piperidine; Diltiazem, 3-(acetyloxy)-5-[2-(dimethylamino)ethyl]-2,3-dihydro-2-(4-methoxyphenyl)-1,5-benzothiazepin-4-(5H)-one; Cyproheptadine, 4-(5H-dibenzo[a,d]cyclohepten-5-ylidene)-1-methylpiperidine, and others. Representative literature disclosing the foregoing compounds in calcium entry blocker activity include D. A. Lowe et al., Br. J. Pharmacol. (1981) 74, 651, P. D. Henry, Am. J. Cardiology, 48 1047 (1980); L. D. Hillis, J. Cardiovasc. Med. 5(6) 583, 1980; and R. A. Janis et al., J. Med. Chem. 26(6), 775 (1983).

Two 4-(5H-dibenzo[a,d]cyclohepten-5-yl)piperidine compounds are identified in U.S. Pat. No. 2,985,660 directed to central stimulants and antispasmodic agents in animals. The compounds named in the patent are 5-(N-methyl-4-piperidyl)-5H-dibenzo[a,d]cycloheptene and 5-(4-piperidyl)-5H-dibenzo[a,d]cycloheptene which also may be named 4-(5H-dibenzo[a,d]-cyclohepten-5-yl)-1-methylpiperidine and 4-(5H-dibenzo[a,d]cyclohepten-5-yl)piperidine, respectively. 4-(5H-Dibenzo[a,d]cyclohepten-5-yl)-1-methylpiperidine is also identified by structural formula in an article by E. L. Engelhardt et al., J. Med. Chem. 8, 829 (1965) concerning the antihistamic properties and antiserotonin properties of cyproheptadine compounds.

All of the compounds of the Engelhardt et al. reference having such activity are compounds in which the piperidine ring and the condensed benzene ring system are joined by a double bond. However, 4-(5H-Dibenzo[a,d]cyclohepten-5-yl)-1-methylpiperidine disclosed in the article as a reduction product is not reported to have properties similar to cyproheptadine. No pharmacological property is taught or suggested.

There has been discovered a new class of compounds related to the two aforementioned compounds which show properties suited for use as therapeutic agents for cardiovascular disorders acting pharmacologically as calcium entry blockers. Most of the members of this class of compounds are novel compounds not heretofore known for any pharmacological utility.

DESCRIPTION OF THE INVENTION

According to the present invention it has been discovered that certain 4-(5H-dibenzo[a,d]cyclohepten-5-yl)piperidine compounds represented by the structural formula:

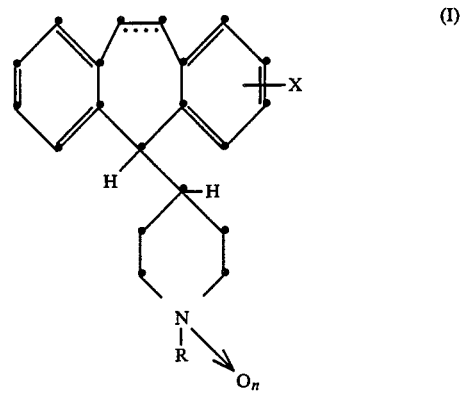

(I)

or a pharmaceutically acceptable acid addition salt thereof, or a hydrate thereof, or compositions containing said compounds are usful for treating cardiovascular disorders caused by high cellular concentration of Ca++. The compounds in which n is 0, are also useful for the preparation of the pharmacologically active N-oxide compounds. In this and succeeding formulas, the ---- bond designation between the 10 and 11 positions indicates that the bond may be a saturated single bond or an unsaturated double bond, X may be hydrogen, halogen, trifluoromethyl or lower alkoxy and R may be hydrogen, lower alkyl or cycloalkyl, and n is 0 or 1. By "lower" is meant a carbon content of from 1 to 6. Suitable cycloalkyl groups are those having from 3 to 6 carbon atoms. "Halogen" includes all of the halogens: fluorine, chlorine, bromine and iodine.

A preferred embodiment of the present invention is that in which the linkage between $C_{10}$ and $C_{11}$ is unsaturated so that the group is —CH=CH— and the substituents are in the 3-position as represented by the following formula:

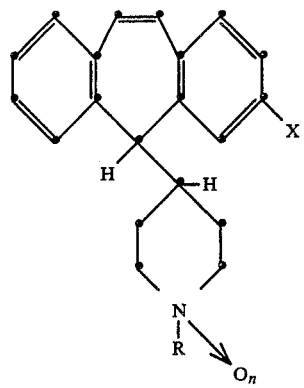
(Ia)

A most preferred embodiment is that embracing compounds of formula Ia when n is 0, and which may be represented by the following formula.

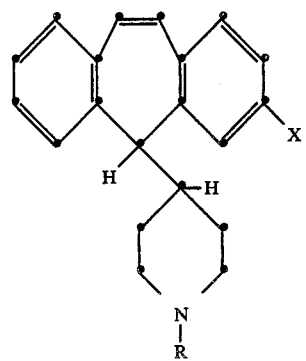
(Ib)

The acid addition salts are those of non-toxic, pharmaceutically acceptable acids and include salts of inorganic acids such as hydrochloric, hydrobromic, hydroiodic, phosphoric, sulfuric, nitric and the like, and organic acids such as acetic, propionic, glycolic, pamoic, pyruvic, malonic, succinic, maleic, fumaric, malic, tartaric, citric, mandelic, benzoic, cinnamic, methanesulfonic, ethanesulfonic, salicylic, p-toluenesulfonic, cyclohexanesulfamic, and the like and include acids related to the pharmaceutically acceptable salts listed in Journal of Pharmaceutical Science, 66, 2 (1977) and incorporated herein by reference.

In view of the non-planar configuration of the compounds in the compositions and methods of the present invention and in view of the presence of a chiral center when X is other than hydrogen, the compounds exist in several isomeric forms. The compounds useful in the compositions and methods of the present invention include the various isomeric forms including mixtures of isomers in various proportions and when the compound is named without designation as to a specific isomer or to a racemic mixture or to a specific mixture of isomers, it is intended to be a generic designation embracing all isomers and mixtures of isomers.

All compounds having the basic structure

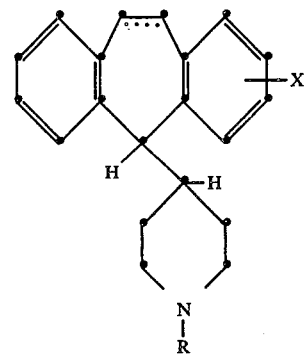

even without further substitution and/or formation of oxide are capable of forming conformational isomers. Isomers have been successfully obtained when R is other than hydrogen and the linkage between $C_{10}$ and $C_{11}$ is unsaturated. When there is a substituent on the dibenzocycloheptene ring (X in Formula I is other than hydrogen) or there is an oxygen on the piperidine nitrogen (n in Formula I is 1), additional isomers may exist. Considering first a compound where X is hydrogen and n is 0, and illustrating with a structure in which the linkage between $C_{10}$ and $C_{11}$ is unsaturated, the two conformational isomers formed may be represented by the following formulas:

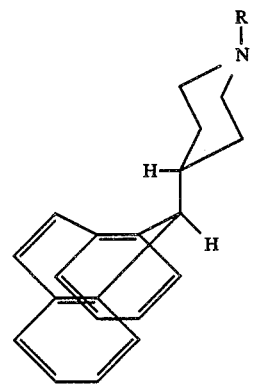
(A)

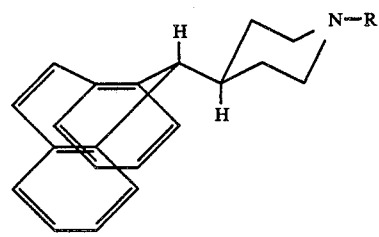
(B)

(A) may be referred to as the equatorial form, then (B) may be designated the axial form. Whether the isomer is to be characterized as equatorial or axial depends on the choice of the reference group at the 5-position. In the present application, the hydrogen (proton) attached to the 5-position is selected as the reference group. When the hydrogen is in equatorial relationship to the four carbons of the dibenzocycloheptene ring system which are common to the cycloheptene and benzene rings, the isomer has been designated as the equatorial isomer. These isomers are obtained by employing different methods of synthesis as hereinafter described. It has been found further that (B) may be converted to (A) by heating but that the reverse conversion does not occur by the application of heat.

When X is other than hydrogen, and n is still 0, not only are there two isomeric forms as a result of restricted conformational mobility

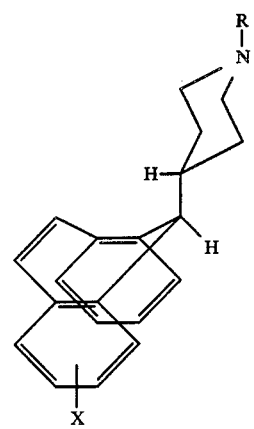
(C)

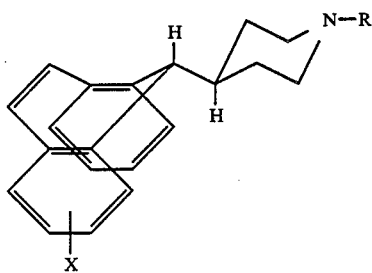
(D)

but there are also enantiomers possible for each of the isomeric forms

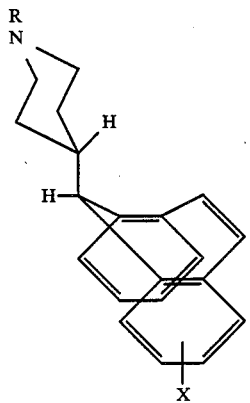
(C')

-continued

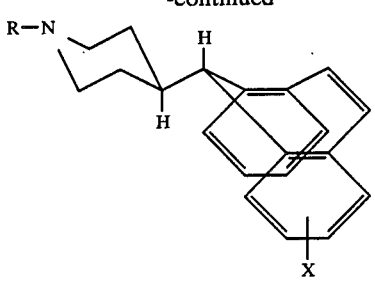
(D')

Thus, (C) and (C') are mirror images and (D) and (D') are mirror images. The enantiomers (C) and (C') have been obtained. The absolute configuration and conformation may be determined by X-ray diffraction methods. The conformational isomers, enantiomers thereof, and their preparation constitutes an aspect of the present invention. Hereinafter, when reference is made generically to the conformational isomers of Formula I, $I_{eq}$ is employed to refer to the equatorial isomer and $I_{ax}$ to refer to the axial isomer.

In addition to the foregoing isomers, when n is 1, there are configurational isomers depending on the position of the oxygen with respect to the piperidine ring. Thus, the oxygen may be positioned in an axial or equatorial relation to the piperidine ring.

The compounds of Formula (I) both as enantiomers and as mixtures of enantiomers, including the acid addition salts, are highly effective as inhibitors of calcium induced contraction of tracheal smooth muscle or vascular tissue. In particular, the compounds in the compositions of the present invention inhibit the contractile properties of smooth muscles and vascular tissue and produce long-lasting dilation of coronary vessels. The effect may be manifest in special vascular regions or in the entire vascular system. Thus, the compounds and the pharmaceutical compositions thereof may be used as vasodilators and are adapted to be employed in the treatment of cardiovascular diseases.

The pharmaceutical compositions of the present invention may contain varying amounts of the 4-(5H-dibenzo[a,d]cyclohepten-5-yl)piperidine compounds of Formula I or the salts thereof depending on whether it is a concentrate composition or treating comosition, and if the latter, depending on the method of administration and further whether it is to be employed as a single dose or as multiple doses.

Although 4-(5H-dibenzo[a,d]cyclohepten-5-yl)-1-methylpiperidine (Formula I, X=H, R=CH$_3$, n=0) and 4-(5H-dibenzo[a,d]cyclohepten-5-yl)piperidine (Formula I, X=H, R=H, n=0) are named in the literature (U.S. Pat. No. 2,985,660; also J. Med. Chem. loc. cit for X=H, R=CH$_3$, n=0), the other active compounds of the compositions and processes of the present invention, namely those compounds of Formula I which fits the qualification that when R is hydrogen or methyl, X is other than hydrogen, are novel compounds which may be prepared, at least in the more stable isomeric form, by methods known to those skilled in the art. Certain of the compounds, may be prepared conveniently by several methods. The preparation of and/or separation of isomers are subsequently described.

The compounds of Formula I may be prepared through a series of reactions hereinafter described in which a 5H-dibenzo[a,d]cyclohepten-5-one represented by the formula;

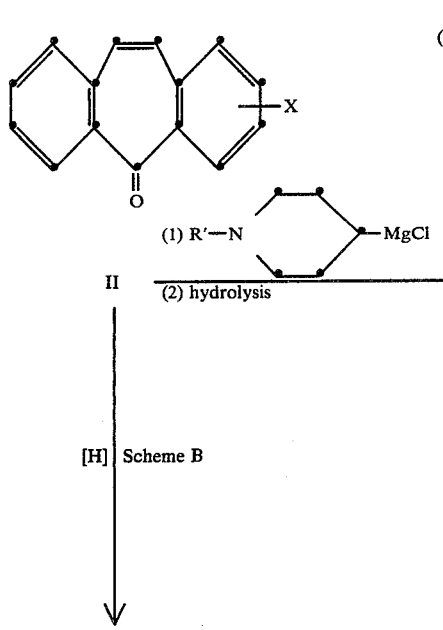

appropriately substituted Grignard reagent to produce the compound of Formula I$_{eq}$. (Scheme B).

The two methods may be seen in the following diagram:

Scheme A

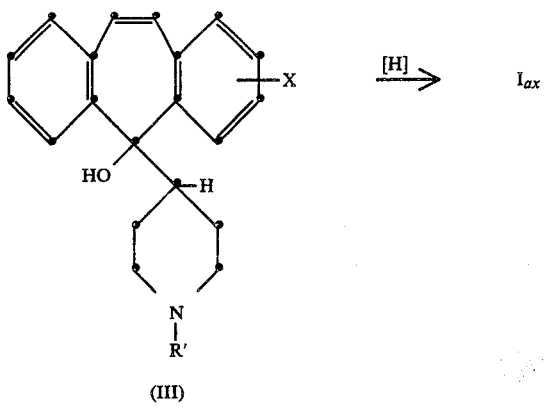

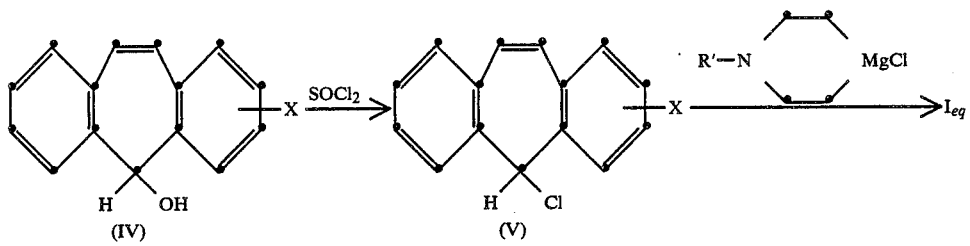

and prepared by a well-established method first described by A. C. Cope et al. (J. Am. Chem. Soc., 73, 1673 (1951) may be considered the ultimate starting material. Many ketones of Formula II are known and in addition, in a number of cases, intermediate compounds produced from the ketone are known. Where known, such intermediate compound may be the starting material.

Proceeding from the ketone, different methods are employed depending on whether R is hydrogen or is an alkyl or cycloalkyl group, and also depending on whether an axial or equatorial isomer is desired. In describing the syntheses, when R is other than hydrogen, the designation R' is employed.

In a method for the preparation of compounds of Formula I when n=0 and R=R', initially at least, in the axial configuration, i.e., I$_{ax}$, the ketone (II) is caused to react with an appropriately substituted piperidine Grignard reagent to produce a hydroxy compound (III) which then is reduced to produce a compound of Formula I$_{ax}$ (Scheme A).

In a method for the preparation of the compounds of Formula I when n=0 and R=R' in the equatorial configuration, i.e., I$_{eq}$, the ketone (II) may be reduced to produce the corresponding hydroxy compound (IV) which then may be converted to the corresponding halide, conveniently the corresponding chloride with thionyl chloride (V), which then is coupled with the appropriately substituted Grignard reagent to produce the compound of Formula I$_{eq}$. (Scheme B).

The condensation between the ketone and Grignard reagent to form the hydroxy compound according to Scheme A is carried out in a conventional Grignard reaction. In carrying out the synthesis, the ketone (II) and the 4-piperidyl Grignard reagent are contacted initially in a portionwise manner, generally by the dropwise addition of an ethereal (preferably tetrahydrofuran) solution of the ketone to an ethereal solution of the Grignard reagent while the mixture is cooled and thereafter allowing the mixture to warm to room temperature to obtain the Mg halide derivative of the hydroxy compound. The reaction mixture is then treated with aqueous acid with cooling to obtain the intermediate compound (III) which may be recovered by conventional procedures.

The reductive cleavage of the hydroxy group in compound (III) may be carried out with triethylsilane with boron trifluoride as catalyst in a solvent such as methylene chloride initially at lowered temperatures (from about −40° to 0° C.), then at ambient temperature. In carrying out the reaction, a molar excess of triethylsilane in a water-immiscible organic solvent is added to a stirred solution of the hydroxy compound (III) in the same solvent, the mixture cooled to −40° to 0° C., and boron trifluoride gas bubbled in for time sufficient to saturate the reaction mixture; thereafter, the reaction mixture is brought gradually to ambient temperature to complete the reduction with the formation of the compound of Formula I in the axial form in the reaction mixture. The reaction is quenched by adding first, solid potassium carbonate, and then water. The product then may be recovered from the organic solution employing conventional procedures.

The product or the organic solution containing the product after appropriate washing and drying but prior to isolation of the product may be subjected to a chromatographic purification procedure carried out on a silica gel column employing pressure and often referred to as Still chromatography or flash chromatography, first described in J. Org. Chem. 43, 2923 (1978). Suitable eluants for this purification include methanol in chloroform or methylene chloride.

In the reaction sequence according to Scheme B, the ketone (II) may be reduced to the corresponding hydroxy compound (IV) employing a molar excess of a reducing agent such as sodium borohydride in a suitable solvent such as a lower alcohol. In carrying out the reaction, sodium borohydride is added portionwise to an alcohol solution of the ketone (II) and the mixture heated at reflux temperature for time sufficient to complete the reaction with the formation of the hydroxy compound (IV). The hydroxy compound then is recovered employing conventional procedures and may be purified by recrystallizing from a suitable solvent such as acetonitrile.

The hydroxy compound (IV) may then be converted to the corresponding halo compound (V), preferably the chloro compound, by reacting with an excess of thionyl chloride in an inert organic solvent such as benzene. In carrying out the reaction, molar excess of thionyl chloride is added to a solution of the hydroxy compound in benzene and the mixture heated at reflux temperature for time sufficient to complete the reaction with the formation of the chloro compound. The excess thionyl chloride and the benzene are codistilled in vacuo to recover the chloro compound (V) as residue. The chloro compound generally may be employed in the next step without purification.

The chloro compound (V) is then coupled with the appropriate 1-alkyl-4-piperidyl Grignard reagent to obtain the compound of Formula I in the equatorial form. In carrying out the reaction, an ethereal solution of the appropriate 4-piperidyl Grignard reagent is added dropwise to a cooled stirred solution of the chloro compound (V) in an ethereal solvent such as tetrahydrofuran. After completion of the addition, the reaction mixture is stirred at ambient temperature preferably for several hours to obtain the desired product $I_{eq}$.

The axial isomers, $I_{ax}$, prepared as above described may be converted to the equatorial isomers, $I_{eq}$, by heating at mildly elevated temperatures, e.g., 90°–100°, either neat or in a polar or non-polar organic solvent such as ethanol, isopropanol, chloroform, benzene, dimethylformamide and the like.

The Grignard reagents of 1-alkyl-4-halopiperidine are generally known compounds. They may be prepared by combining a 1-alkyl-4-halopiperidine with magnesium, preferably in tetrahydrofuran as taught in U.S. Pat. No. 3,014,911.

A still further preparative method is the preparation first of the compound of Formula I in which R is H and n is 0, thereafter alkylating at the nitrogen by conventional procedures, with alkyl halide or by employing reductive alkylation with a ketone or aldehyde.

The preparation of the compound of Formula I in which R is H and n is 0 is carried out by first preparing an N-methylpiperidine compound, causing said N-methylpiperidine compound to react with cyanogen bromide to produce an intermediate cyanamide compound, thereafter subjecting said cyanamide compound to acid hydrolysis and decarboxylation according to the following scheme:

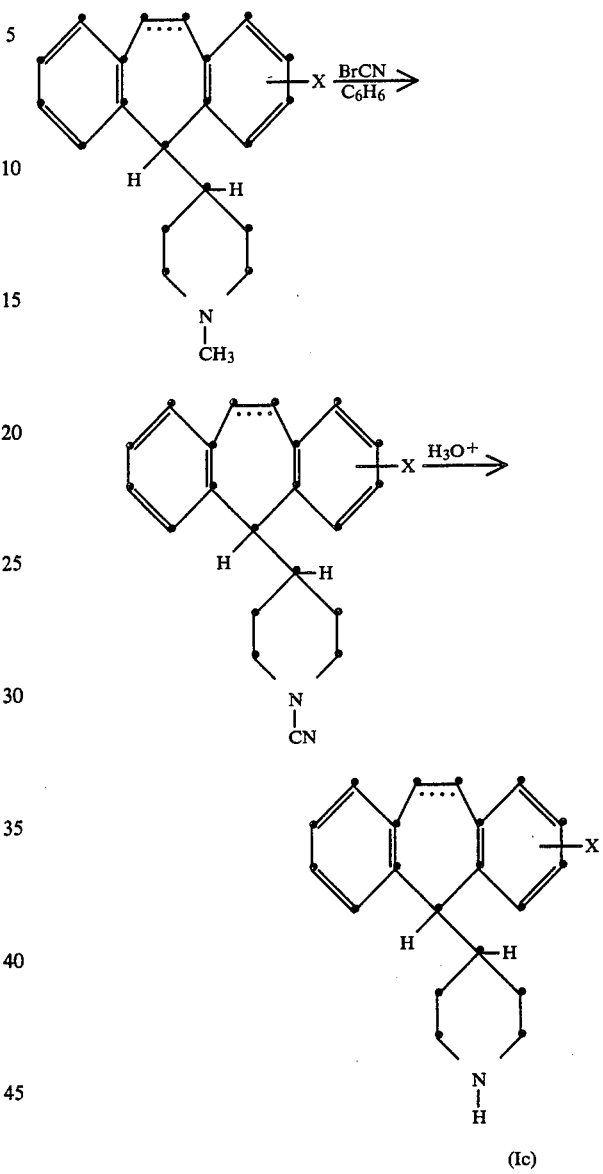

In carrying out the preparation, a solution of the appropriate 4-(5H-dibenzo[a,b]cyclohepten-5-yl)-1-methylpiperidine compound in an inert solvent such as benzene is added dropwise to a stirred solution of cyanogen bromide in the same solvent while under an atmosphere of nitrogen. After completion of the addition, stirring is continued for several hours to obtain a cyanamide compound which is recovered from the reaction mixture by first evaporating the solvent to obtain a residue, dissolving the residue in a water-immiscible organic solvent, washing the solution by conventional procedures, drying, filtering and concentrating to obtain the cyanamide reaction product substantially freed of reactants. The cyanamide compound, thus purified, then is subjected to hydrolysis and decarboxylation which may be carried out by adding it to a 50:50 mixture of 6N hydrochloric acid and glacial acetic acid and heating at reflux temperature for about 10 to 20 hours to obtain the desired compound of Formula Ic in the reaction mixture. The compound of Formula Ic then may be recovered by concentrating in vacuo to obtain a solid which then may be purified by conventional procedures such as partitioning between aqueous alkali and ethyl acetate, drying the ethyl acetate solution, and evaporating the solvent and obtaining the product as residue. The latter may be further purified by conventional procedures such as recrystallization.

The N-unsubstituted piperidine compound of Formula Ic may be employed as such or may be alkylated. In one method, the compound of Formula Ic is caused to react with an alkyl halide in the presence of a hydrogen halide acceptor to obtain a compound of Formula I in which R is alkyl. In carrying out the reaction, the appropriate alkyl halide may be added to a solution of an N-unsubstituted piperidine compound of Formula Ic in an inert organic solvent in the presence of a hydrogen halide acceptor and the mixture stirred, usually with warming, to obtain the desired compound of Formula I wherein R is alkyl. The product may then be recovered and purified, if desired, by conventional procedures.

The N-unsubstituted piperidine compound of formula Ic also may be reductively alkylated according to the following scheme:

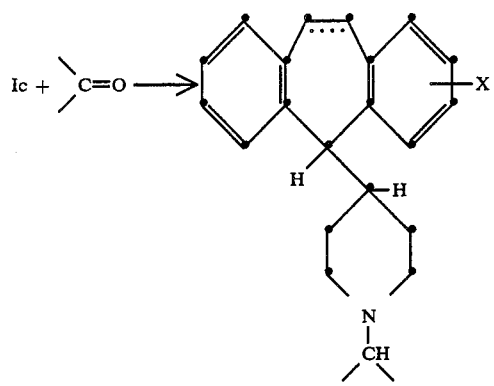

In the foregoing equation, >C=O represent an appropriate aldehyde or ketone which or reductive alkylation forms the >CH-group corresponding to R'. The reductive alkylation may be carried out by causing a 4-(5H-dibenzo[a,d]cyclohepten-5-yl)piperidine compound (Ic) to react with excess carbonyl compound and aluminum amalgam in a polar solvent such as methanol with warming, usually at least overnight, thereafter recovering the product from the filtrate after first removing aluminum and mercury salts. Reductive alkylation procedure is especially useful when R is secondary alkyl group since many ketones are frequently more readily available than branched alkyl halides.

The oxides (n=1 in Formula I) may be prepared by causing the appropriate 4-(5H-dibenzo[a,d]cyclohepten-5-yl)piperidine compound to react with a large molar excess of a peroxide, preferably, hydrogen peroxide in a solvent such as methanol at ambient temperature for time sufficient to complete the reaction. The reaction may take from 24 to 48 hours. Determination of completion of the reaction may be made by thin layer chromatographic analysis (TLC). When the reaction is substantially complete, the unreacted peroxide may be decomposed, e.g. with platinum on carbon, and the product separated from the catalyst and recovered and purified according to conventional procedures.

Enantiomers are possible when X in Formula I is other than hydrogen and R is R', i.e., when it is a nuclear substituted-N-alkylpiperidine compound. These enantiomers may be obtained employing conventional resolution methods. While enantiomers are possible for each of the conformational isomers, difficulty may be encountered in resolving certain of the compounds depending on the stability of the particular conformational isomer to conditions encountered in current resolution methods. Thus, in some cases, one conformational isomer will be converted to the other isomer with the resolved product being the enantiomorphic form of the converted isomer rather than that sought to be obtained. Enantiomers of the equatorial isomer have been found to be the ones more readily obtainable.

In preparing the enantiomers, the cycloheptene-ring-substituted-N-alkylpiperidine compound may be mixed with (1)-tartaric acid or other appropriate resolving acid whereupon the (1)-tartrate salt of one of the enantiomers separates in the reaction mixture. The salt is removed by filtration, purified and then admixed with a mild inorganic base such as saturated sodium bicarbonate to obtain one of the enantiomers as a free base which then may be recovered from the medium by conventional procedures such as extracting with a water-immiscible solvent and recovering therefrom. The filtrate from the initial reaction with (1)-tartaric acid or other resolving acid is converted first to a free base and the latter treated with (d)-tartaric acid or other appropriate resolving acid to obtain the salt thereof. The salt is purified employing conventional procedure and then converted to a free base also employing conventional procedures.

All of the compounds of Formula I may be obtained as acid addition salts. Some of the products of the present invention are preferably isolated as acid addition salts. In other cases, they may be isolated as bases and converted into salts as desired. When salts are desired, the base product may be dissolved in a solvent such as alkanol and the appropriate acid added thereto. Usually the crystalline salt will start to form immediately and precipitate in the reaction mixture. The reaction mixture may be cooled to facilitate and/or complete the reaction.

The usefulness of the compounds in the compositions of the present invention as calcium entry blockers may be demonstrated by the ability of the compounds to induce contraction of tracheal smooth muscle or of vascular tissue. The property may be observed in a test in which segments of vascular smooth muscle obtained from male Sprague-Dawley rats are suspended in physiological salt solution in a tissue bath instrumented for recording contractions. After the tissue has been equilibrated, washed in calcium-free physiological salt solution and then depolarized, 1.0 mM calcium chloride is re-added to induce contraction. After the contraction has reached a plateau, tissues are washed and a test compound or vehicle is added to determine the effect on a second contraction achieved by the above cyclic protocol. From measuring the initial contraction as well as the second contraction in the presence of the test compound, the extent of inhibition may be calculated. The results of these tests for representative compounds in the compositions of the present invention are seen in the following table. The results are with tests conducted at very low concentrations of $10^{-7}M$ or less.

| Active Component | Percent Inhibition of Rat Aorta |
|---|---|
| 5H—eq 4-(5H—Dibenzo[a,d]cyclohepten-5-yl)-piperidine | 39% at $10^{-7}$ M |
| 5H—eq 4-(5H—Dibenzo[a,d]cyclohepten-5-yl)-1-methylpiperidine* | 11% at $10^{-8}$ M |
| 5H—ax 4-(5H—Dibenzo[a,d]cyclohepten-5-yl)-1-methylpiperidine | 30% at $10^{-7}$ M |
| 5H—eq (±)4-(3-Bromo-5H—dibenzo[a,d]cyclohepten-5-yl)-1-methylpiperidine | 80% at $10^{-7}$ M |
| 5H—eq (+)4-(3-Bromo-5H—dibenzo[a,d]cyclohepten-5-yl)-1-methylpiperidine | 22% at $10^{-7}$ M |
| 5H—eq (−)4-(3-Bromo-5H—dibenzo[a,d]cyclohepten-5-yl)-1-methylpiperidine | 92% at $10^{-7}$ M |
| 5H—ax (±)4-(3-Bromo-5H—dibenzo[a,d]cyclohepten-5-yl)-1-methylpiperidine | 79% at $10^{-7}$ M |
| 5H—eq (±)4-(3-Methoxy-5H—dibenzo[a,d]cyclohepten-5-yl)-1-methylpiperidine | 37% at $10^{-8}$ M |
| 5H—eq 4-(5H—Dibenzo[a,d]cyclohepten-5-yl)-1-isopropylpiperidine | 44% at $10^{-7}$ M |
| 5H—eq 4-(5H—Dibenzo[a,d]cyclohepten-5-yl)-1-cyclohexylpiperidine | 48% at $10^{-7}$ M |
| 5H—eq 4-(5H—Dibenzo[a,d]cyclohepten-5-yl)-1-methylpiperidine-1-oxide | 17% at $10^{-7}$ M |

*Compound previously prepared as described in J. Med. Chem. 8, 829, 835 (1965).

The process of the present invention comprises administering to subjects with cardiovascular disorders caused by high cellular concentration of Ca++, a therapeutically effective amount of a 4-(5H-dibenzo[a,d]cyclohepten-5-yl)piperidine compound of Formula I or a pharmaceutically acceptable acid addition salt thereof, or compositions containing said compounds. In general, the daily dose may be that to provide between about 0.3 and 40 mg/kg/day, preferably in the range 1.0 mg/kg/day and 12 mg/kg/day while considering patients' health, weight, age, and other factors which influence response to a drug as well as the particular drug to be employed. Further, since the drug is useful in several aspects of cardiovascular therapy, the dose is also dependent on the particular disease to be alleviated. The drug may be administered orally or parenterally or by any other means, and in a single unit or in a number of smaller units given during the period of a day in compositions hereinafter detailed.

The pharmaceutical compositions of the present invention comprises a 4-(5H-dibenzo[a,d]cyclohepten-5-yl)piperidine compound of Formula I or a pharmaceutically acceptable acid addition salt thereof in intimate admixture with a pharmaceutically acceptable carrier. The optically active products within the structure of Formula I and mixtures thereof, and their salts also can be prepared in pharmaceutical formulations suitable for oral or parenteral administration in much the same manner as optically inactive compounds.

The carrier may take a wide variety of forms depending on the form of preparation desired for administration, e.g., oral or parenteral. In compositions for oral administration, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparation such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed.

It is especially advantageous to formulate the pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit form are tablets, capsules, pills, powder packets, wafers, teaspoonfuls, tablespoonfuls and the like, and segregated multiples thereof. The amount of active ingredient per dosage unit will be from about 0.075 mg. to about 10 mg. Preferably, the amount of active ingredient would be from about 0.3 to about 4 mg.

The following examples illustrate the invention but are not to be construed as limiting.

Examples I–XV illustrate the preparation of the compounds for the compositions and methods of the present invention.

EXAMPLE I 4-(3-Bromo-5H-dibenzo[a,d]cyclohepten-5-yl)-1-methylpiperidine, equatorial isomer

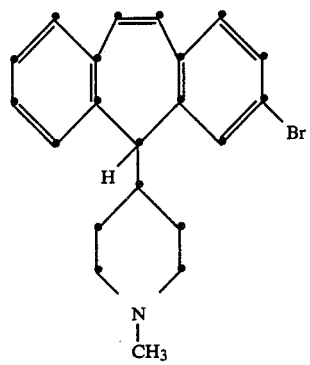

12.8 grams (0.11 mole) of thionyl chloride was added to a solution of 24.6 grams (0.086 mole) of 3-bromo-5H-dibenzo[a,d]cyclohepten-5-ol in 750 milliliters of benzene and the resulting mixture heated at reflux temperature for two hours. At the end of this period, the mixture was cooled, concentrated to dryness in vacuo to obtain 24.3 grams of 3-bromo-5-chloro-5H-dibenzo[a,d]cycloheptene intermediate compound.

The chloro intermediate thus obtained was dissolved in 150 milliliters of tetrahydrofuran and cooled in an ice bath. To the cooled solution was added dropwise with stirring, 210 milliliters of 0.49M 1-methyl-4-piperidylmagnesium chloride (Grignard) solution in tetrahydrofuran. After completion of the addition, the ice bath was removed and the mixture stirred at room temperature for 3 hours. Thereafter, the solvent was removed in vacuo and toluene and water added to the residue. The toluene solution was washed three times with water, then with saturated sodium chloride solution, and thereafter dried over magnesium sulfate. The toluene then was vaporized in vacuo and the remaining concentrate chromatographed through a Still column employing 3 percent methanol in chloroform as eluant. Fractions containing fairly clean product were combined and the solvent vaporized to obtain a solid residue which after recrystallization from acetonitrile amounted to 3.8 grams of 4-(3-bromo-5H-dibenzo[a,d]cyclohepten-5-yl)-1-methylpiperidine product, m.p. 146°–146.5° C. The compound was determined by NMR analysis to be the 5H-equatorial form. Elemental analyses were as follows:

Calcd. for $C_{21}H_{22}BrN$: C, 68.48; H, 6.02; N, 3.80. Found: C, 68.82; H, 6.12; N, 3.70.

The 3-bromo-5H-dibenzo[a,d]cyclohepten-5-ol starting material was obtained from an earlier preparation in which 30.8 grams of 3-bromo-5H-dibenzo[a,d]cyclohepten-5-one was reduced with 8.6 grams of sodium borohydride by adding a solution of the sodium borohydride in 100 milliters of water to a solution of the ketone in 600 millititers of methanol at reflux temperature, thereafter evaporating most of the methanol to obtain the alcohol as a solid, then recovering the latter by filtration, then washing and drying in vacuo. A sample of the 3-bromo-5H-dibenzo[a,d]cyclohepten-5-ol when recrystallized from acetonitrile and dried at 78° C. at 0.1 mm Hq over phosphorus pentoxide for three hours had a melting point of 154°–146° C.

EXAMPLE II

Resolution of (±)-4-(3-bromo-5H-dibenzo[a,d]cyclohepten-5-yl)-1-methylpiperidine 2.78 grams (7.55 moles) of (±)-4-(3-bromo-5H-dibenzo[a,d]cyclohepten-5-yl)-1-methylpiperidine and 1.13 grams (0.00755 mole) of (1)-tartaric acid were mixed together and dissolved in 160 milliliters of boiling water. The resulting mixture was filtered to clarify the solution and then was allowed to cool slowly whereupon crystals of an (1)-tartaric acid salt of one of the isomers separated in the reaction mixture. The crystals were recovered by filtration, washed with water and dried to obtain 0.87 gram of a salt having melting point of 232°–234° C. and $[\alpha]_{589}^{25}$ −31.6° (c 1.847, pyridine). The combined filtrate and washings were concentrated to approximately 90 milliliters, then allowed to cool to obtain an additional 0.26 gram of a salt having a melting point of 228°–232° C., $[\alpha]_{589}^{25}$ −30.0° (c 1.122, pyridine). The crystallized salts were combined and used in Step A; and the filtrates and washings were combined, evaporated to dryness and used in Step B.

Step A:
(+)-4-(3-bromo-5H-dibenzo[a,d]cyclohepten-yl)-1-methylpiperidine 1.13 grams of the crystalline salt prepared as above described was recrystallized twice from water to obtain 0.67 gram of a purified salt having a constant rotation, $[\alpha]_{589}^{25}$ of −34.6° (c 1.641, pyridine) and a melting point of 239°–239.5° C. The salt was intimately admixed with saturated sodium bicarbonate solution to obtain a free base, and the resulting base mixture extracted with ether. The ether solution was washed with water, dried over magnesium sulfate, then filtered, and the ether vaporized to obtain a purified solid base. The solid was recrystallized from acetonitrile to obtain (+)-4-(3-bromo-5H-dibenzo[a,d]cyclohepten-5-yl)-1-methylpiperidine, m.p. 178°–180° C.; $[\alpha]_{589}^{25}$ +26.9° $[\alpha]_{578}^{25}$ +29.0°, $[\alpha]_{546}^{25}$ +37.2°, $[\alpha]_{436}^{25}$ +126° (c 0.583, $CHCl_3$). Elemental analyses were as follows:

Calculated for $C_{21}H_{22}BrN$: C, 68.48; H, 6.02; N, 3.80. Found: C, 68.50; H, 6.15; N, 4.07.

Step B:
(−)-4-(3-bromo-5H-dibenzo[a,d]cyclohepten-5-yl)-1-methylpiperidine

The residue obtained by evaporating the filtrates and washings as described above was suspended in water and then admixed with saturated sodium carbonate solution. The resulting mixture was extracted with ether to obtain 0.85 gram of free base. This base and 0.346 gram of d-tartaric acid were dissolved in 26 milliliters of boiling water. The solution then was allowed to cool whereupon a crystalline solid formed which on recovery amounted to 0.56 gram of a salt of m.p. 231°–234° C. and $[\alpha]_{589}^{25}$ +28.0° (c 1.38, pyridine). The salt was recrystallized twice from water to obtain 0.26 gram of purified (−)-4-(3-bromo-5H-dibenzo[a,d]cyclohepten-5-yl)-1-methylpiperidine d-tartaric acid salt, m.p. 239°–239.5° C. and constant rotation of $[\alpha]_{589}^{25}$ +34.1° (c 1.586, pyridine).

The salt was converted to a free base by intimately admixing with saturated sodium bicarbonate solution and extracting the resulting mixture with ether, drying and evaporating the ether solution in a manner similar to that described in Step A. The base thus obtained was recrystallized from acetonitrile to obtain (−)-4-(3-bromo-5H-dibenzo[a,d]cyclohepten-5-yl)-1-methylpiperidine product, m.p. 178°–180° C.; $[\alpha]_{589}^{25}$ −27.4°, $[\alpha]_{578}^{25}$ −29.5°, $[\alpha]_{546}^{25}$ −38.0°, $[\alpha]_{436}^{25}$ −127° (c 0.559, $CHCl_3$). Elemental analyses were as follows:

Calculated for $C_{21}H_{22}BrN$: C, 68.48; H, 6.02; N, 3.80. Found: C, 68.46; H, 6.24; N, 3.87.

EXAMPLE III 4-(3-Bromo-5H-dibenzo[a,d]cyclohepten-5-yl)-1-methylpiperidine, axial isomer 1 gram (8.6 millimoles) of triethylsilane in 10 milliliters of methylene chloride was added with stirring to 2 grams (0.0055 mole) of 4-(3-bromo-5-hydroxy-5H-dibenzo[a,d]cyclohepten-5-yl)-1-methylpiperidine in 100 milliliters of methylene chloride. The mixture was cooled to 0° C., boron trifluoride bubbled thereinto for about 12 minutes, then maintained at 0° C. with stirring for five hours. Thereafter, the mixture was allowed to warm to room temperature and the reaction quenched by adding first, solid potassium carbonate and then water. The aqueous and methylene chloride layers were separated and the latter washed twice with water and with saturated sodium chloride solution. The washed solution was dried over magnesium sulfate and the dried solution chromatographed on a Still column employing initially 3 percent methanol/methylene chloride as eluant to elute 4-(3-bromo-5H-dibenzo[a,d]cyclohepten-5-ylidene)-1-methylpiperidine byproduct and thereafter, 5 percent methanol/methylene chloride to elute 4-(3- bromo-5H-dibenzo[a,d]-cyclohepten-5-yl)-1-methylpiperidine product. The fractions containing the product were placed under reduced pressure to evaporate the solvent and to recover the product as residue. The residue was dried at 50° C. for 24 hours; it amounted to 0.53 gram. NMR spectrum of the product indicated it to be different from but isomeric with the compound of Example I and to be the 5H-axial form. Elemental analyses of the product were as follows:

Calcd. for $C_{21}H_{22}BrN$: C, 68.48; H, 6.02; N, 3.80. Found: C, 68.59; H, 6.19; N, 3.89.

The 4-(3-bromo-5-hydroxy-5H-dibenzo[a,d]cyclohepten-5-yl)-1-methylpiperidine compound employed as starting material was obtained from an earlier preparation in which a tetrahydrofuran solution of Grignard reagent obtained from 25.5 grams of magnesium, 141 grams of 1-methyl-4-chloropiperidine and 200 milliliters of tetrahydrofuran was added with cooling and stirring to a solution of 25.0 grams of 3-bromo-5H-dibenzo[a,d]cyclohepten-5-one in 250 milliliters of tetrahydrofuran. After the completion of the addition, the mixture was stirred at room temperature for several hours then the tetrahydrofuran solvent distilled in vacuo to obtain a residue. The residue was dissolved in a biphasic mixture of benzene and water, the benzene solution separated, washed with water, brine, dried over magnesium sulfate, filtered and the solvent evaporated in vacuo to obtain 4-(3-bromo-5-hydroxy-5H-dibenzo[a,d]cyclohepten-5-yl)-1-methylpiperidine compound as residue.

EXAMPLE IV 4-(5H-Dibenzo[a,d]cyclohepten-5-yl)-1-methylpiperidine, axial isomer

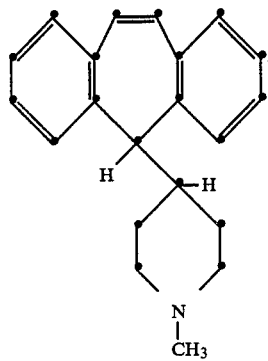

1.2 grams (0.0103 mole) of triethylsilane was added with stirring to 2 grams (0.0065 mole) of (5-hydroxy-5H-dibenzo[a,d]cyclohepten-5-yl)-1-methylpiperidine in 150 milliliters of methylene chloride. The reaction mixture was then cooled to −35° C. and boron trifluoride gas bubbled in. The reaction mixture turned a deep red with red precipitate. The mixture was maintained at −20° C. for about 3 hours and then at about −10° C. for about 3 hours. Most of the red precipitate was gone by the end of this period. The methylene chloride solution was then concentrated to dryness and the residue triturated with acetonitrile. The undissolved solid was filtered and the filtrate dried over phosphorus pentoxide at reduced pressure. The dried material was chromatographed through a Still column employing 5 percent methanol/methylene chloride as eluant. The residue was recovered from the elution in the usual way was subjected to several dryings. After a final drying at 40° C./0.2 mm. Hg over phosphorus pentoxide for 20 hours, a purified 4-(5H-dibenzo[a,d]cyclohepten-5-yl)-1-methylpiperidine product, m.p. 127° C. was obtained. Elemental analyses for the product were as follows:

Calculated for $C_{21}H_{23}N$: C, 87.15; H, 8.01; N, 4.84. Found: C, 87.28; H, 8.27; N, 5.07.

The product is different from but isomeric with the product prepared as described in J. Med. Chem. 8, 829,835 (1965) and in Example XV.

EXAMPLE V 4-(3-Methoxy-5H-dibenzo[a,d]cyclohepten-5-yl)-1-methylpiperidine

A cooled solution of 5.4 grams (0.021 mole) of 5-chloro-3-methoxy-5H-dibenzo[a,d]cycloheptene in 60 milliliters of tetrahydrofuran was added dropwise under an atmosphere of nitrogen to 50 milliliters of a cooled solution of 0.49M 1-methyl-4-piperidylmagnesium chloride in tetrahydrofuran (Grignard solution) over a period of about 40 minutes. After completion of the addition, the mixture was stirred at room temperature for 2 hours and then at reflux temperature for fifteen minutes. The reaction mixture was then cooled and the product recovered from the reaction mixture by concentrating the mixture in vacuo to dryness, adding toluene to dissolve the organic product, filtering off the magnesium, and then separating, washing and drying the toluene solution in a manner similar to that described in Example I. The toluene was vaporized from the dried solution to obtain a residue which was dissolved in acetonitrile, recrystallized therefrom and the crystals dried at 78° C./0.2 mm. Hg over phosphorus pentoxide for four hours to obtain the desired 4-(3-methoxy-5H-dibenzo[a,d]cyclohepten-5-yl)-1-methylpiperidine product, m.p. 122°–23° C. Elemental analyses were as follows:

Calculated for $C_{22}H_{25}NO$: C, 82.72; H, 7.89; N, 4.39. Found: C, 82.43; H, 8.09; N, 4.09.

The 5-chloro-3-methoxy-5H-dibenzo[a,d]cycloheptene starting material was prepared from 3-hydroxy-5H-dibenzo[a,d]cyclohepten-5-one by methylation at the hydroxy, reduction of the ketone to an alcohol and converting the alcohol to a chloro compound in the following manner:

(a) 6.67 grams (0.03 mole) of 3-hydroxy-5H-dibenzo[a,d]cyclohepten-5-one was caused to react with 5.7 grams (0.045 mole) of dimethyl surfate in the presence of 1.8 grams (0.045 mole) of sodium hydroxide in 20 milliliters of water, first at 5°–10° C. and thereafter at 75°–78° C. with the formation of 3-methoxy-5H-dibenzo[a,d]cyclohepten-5-one intermediate. The latter was recovered by extracting from the reaction mixture with benzene, washing the benzene solution with water and brine, drying over magnesium sulfate, filtering the drying agent and concentrating in vacuo to obtain 6.4 grams of residue.

(b) The 3-methoxy-5H-dibenzo[a,b]cyclohepten-5-one intermediate (6.4 grams, 0.027 mole) was dissolved 140 milliliters of methanol and added to and caused to react with a solution of 2.57 grams (0.0678 mole) of sodium borohydride in 29 milliliters of water and 0.1 milliliter of 10N sodium hydroxide at reflux temperature to obtain 3-methoxy-5H-dibenzo[a,d]cyclohepten-5-ol intermediate which was recovered by vaporizing some of the methanol in vacuo and chilling to obtain a solid which after filtering and drying amounted to 5.3 grams.

(c) The 3-methoxy-5H-dibenzo[a,d]cyclohepten-5-ol thus obtained was dissolved in 200 milliliters of benzene and the solution saturated with hydrogen chloride gas to obtain the 5-chloro-3-methoxy-5H-dibenzo[a,d]cycloheptene which was recovered in an amount of 5.4 grams by evaporating the solvent in vacuo after first removing the water by-product with calcium chloride.

EXAMPLE VI 4-(5H-Dibenzo[a,d]cyclohepten-5-yl)piperidine

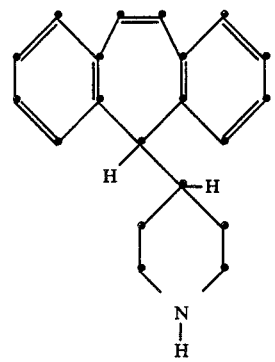

A solution of 2.89 grams (0.01 mole) of 4-(5H-dibenzo[a,d]cyclohepten-5-yl)-1-methylpiperidine in 75 milliliters of methylene chloride was added dropwise over a 1 hour period in an atomsphere of nitrogen to a solution of 1.6 grams (0.015 mole) of cyanogen bromide in 20 milliliters of benzene. The reaction mixture was allowed to stir overnight to obtain 1-cyano-4-dibenzo[a,d]cyclohepten-5-yl)piperidine. The solvent then was evaporated and the residue dissolved in 100 milliliters of methylene chloride, washed successively with 2N hydrochloric acid and saturated sodium chloride solution and dried over magnesium sulfate. The latter was filtered and the solvent evaporated to recover 1-cyano-4-(5H-dibenzo[a,d]cyclohepten-5-yl)piperidine.

30 milliliters of 6N hydrochloric acid and 30 milliliters of glacial acetic acid was added to the latter and the mixture heated and stirred at reflux temperature for 24 hours. At the end of this period the mixture was evaporated to dryness in vacuo and the residue partitioned between aqueous sodium carbonate solution and chloroform. The resulting chloroform solution was separated from the biphasic mixture, dried over magnesium sulfate, the filtered, and the filtrate evaporated to dryness to obtain a 4-(5H-dibenzo[a,d]cyclohepten-5-yl)piperidine product as residue which became crystalline after acetonitrile trituration. The crude crystalline product was purified by Still chromatography employing 10 percent methanol in chloroform as eluant, followed by recrystallization from acetonitrile. The purified product after drying at 78° C./0.1 mm Hg had a melting point of 152°-153° C. Elemental analyses were as follows:

Calcd for $C_{20}H_{21}N$: C, 87.22; H, 7.69; N, 5.09. Found: C, 87.17; H, 8.01; N, 5.30.

EXAMPLE VII 4-(5H-Dibenzo[a,d]cyclohepten-5-yl)-1-isopropylpiperidine

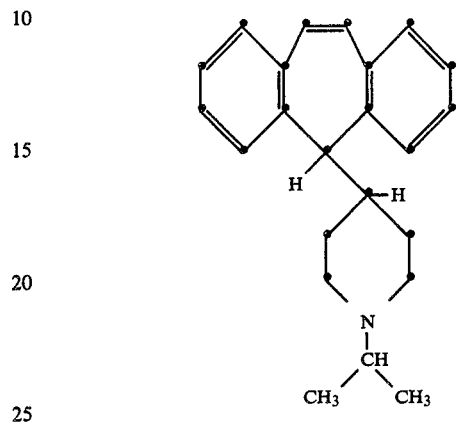

0.50 gram (1.8 millimoles) of 4-(5H-dibenzo[a,d]cyclohepten-5-yl)piperidine (prepared in a manner described in the preceding example), 3.96 grams (68.1 millimoles) of acetone and 5 milliliters of methanol were warmed gently to start dissolution. To this was added 0.30 gram (11 millimoles) of aluminum bits and a catalytic amount (0.01 gram; 0.04 millimole) of mercuric chloride and the resulting mixture stirred for 2.5 hours. A TLC analysis of the reaction mixture showed presence of some but minor amount of product. The mixture was stirred for 48 hours. A TLC analysis at this time (1 percent methanol/99 percent chloroform saturated with ammonia) indicated consumption of the starting material with the formation of a new product which was determined by $^1$H NMR to be a 4-(5H-dibenzo[a,d]cyclohepten-5-yl)-1-isopropylpiperidine product. The reaction mixture was filtered through a pad of celite and the solvent removed in vacuo to obtain a residue which after recrystallization from a minimum amount of hot acetonitrile and drying for 3.5 hours at 100° C./1 mm. Hg, was a white powder, m.p. 124°-126° C. The product had elemental analyses as follows:

Calculated for $C_{23}H_{27}N$: C, 87.20; H, 8.57; N, 4.41. Found: C, 87.10; H, 8.85; N, 4.61.

EXAMPLE VIII

4-(5H-Dibenzo[a,d]cyclohepten-5-yl)-1-cyclohexylpiperidine

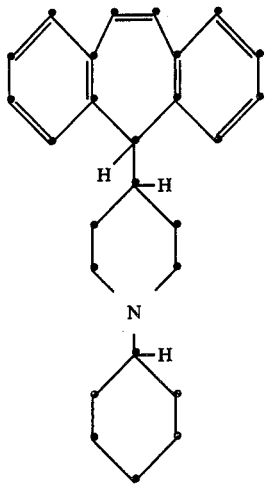

0.50 gram (1.8 millimoles) of 4-(5H-dibenzo[a,d]cyclohepten-5-yl)piperidine, 6.68 gram (68.1 millimoles) of cyclohexanone, 0.49 gram of finely cut bits of aluminum foil and 15 milliliters of methanol were mixed together. To the mixture, 0.01 gram (0.04 millimole) of mercuric chloride was added and the resulting mixture stirred at ambient temperature for 24 hours at which time a TLC analysis indicated complete consumption of the starting material and formation of a new product. The reaction mixture was filtered successively through celite and silica gel to remove aluminum and mercury salts and the filtrate concentrated in vacuo to obtain a yellow oil which crystallized on trituration with acetonitrile. Recrystallization from acetonitrile produced purified 4-(5H-dibenzo[a,d]cyclohepten-5-yl)-1-cyclohexylpiperidine product as long, straw-colored needles of melting point 162°–164° C. in a yield of 490 milligrams (75 percent). Elemental analyses were as follows:

Calculated for $C_{26}H_{31}N$: C, 87.34; H, 8.74; N, 3.92. Found: C, 87.22; H, 9.14; N, 4.26.

EXAMPLE IX

In reductive alkylation reactions employing aluminum and mercuric chloride and carried out in a manner similar to that described in Examples VII and VIII, the following compounds may be prepared: 4-(5H-Dibenzo[a,d]cyclohepten-5-yl)-1-cyclopentylpiperidine from 4-(5H-dibenzo[a,d]cyclohepten-5-yl)piperidine and cyclopentanone.

4-(2-Bromo-5H-dibenzo[a,d]cyclohepten-5-yl)-1-cyclopentylpiperidine from 4-(2-bromo-5H-dibenzo[a,d]cyclohepten-5-yl)piperidine and cyclopentanone.

4-(3-Isopropoxy-5H-dibenzo[a,d]cyclohepten-5-yl)-1-cyclopentylpiperidine from 4-(3-isopropoxy-5H-dibenzo[a,d]cyclohepten-5-yl)piperidine and cyclopentanone.

4-(3-Chloro-5H-dibenzo[a,d]cyclohepten-5-yl)-1-cyclohexylpiperidine from 4-(3-chloro-5H-dibenzo[a,d]cyclohepten-5-yl)piperidine and cyclohexanone.

4-(3-Ethoxy-5H-dibenzo[a,d]cyclohepten-5-yl)-1-cyclohexylpiperidine from 4-(3-ethoxy-5H-dibenzo[a,d]cyclohepten-5-yl)piperidine and cyclohexanone.

4-(1-Methoxy-5H-dibenzo[a,d]cylclohepten-5-yl)-1-(3-pentyl)piperidine from 4-(1-methoxy-5H-dibenzo[a,d]cyclohepten-5-yl)piperidine and diethylketone.

4-(3-Chloro-5H-dibenzo[a,d]cyclohepten-5-yl)-1-(2-butyl)piperidine from 4-(3-chloro-5H-dibenzo[a,d]cyclohepten-5-yl)piperidine and methyl ethyl ketone.

4-(3-Bromo-10,11-dihydro-5H-dibenzo[a,d]cyclohepten-5-yl)-1-isopropylpiperidine from 4-(3-bromo-10,11-dihydro-5H-dibenzo[a,d]-cyclohepten-5-yl)piperidine and acetone.

4-(3-(n-Propoxy)-10,11-dihydro-5H-dibenzo[a,d]cyclohepten-5-yl)-1-cyclohexylpiperidine from 4-(3-(n-propoxy)-10,11-dihydro-5H-dibenzo[a,d]cyclohepten-5-yl)-piperidine and cyclohexanone.

4-(1-Methoxy-10,11-dihydro-5H-dibenzo[a,d]cyclohepten-5-yl)-1-cyclopentylpiperidine from 4-(1-methoxy-9,10-dihydro-5H-dibenzo[a,d]cyclohepten-5-yl)piperidine and cyclopentanone.

4-(2-Chloro-10,11-dihydro-5H-dibenzo[a,d]cyclohepten-5-yl)-1-(2-butyl)piperidine from 4-(2-chloro-10,11-dihydro-5H-dibenzo[a,d]cyclohepten-5-yl)piperidine and methyl ethyl ketone.

EXAMPLE X

In operations carried out in a manner similar to that described in Example I, an appropriate 5-chloro-5H-dibenzo[a,d]cycloheptene compound is first prepared by the reaction of thionyl chloride on an appropriate 5H-dibenzo[a,d]cyclohepten-5-ol which in turn is prepared from the corresponding ketone, and the 5-chloro intermediate thus obtained employed in a coupling reaction with an appropriate 1-alkyl-substituted-4-piperidylmagnesium chloride in ethereal solution.

In such operation, the following compounds may be prepared:

4-(3-Fluoro-5H-dibenzo[a,d]cyclohepten-5-yl)-1-(n-butyl)piperidine from 3-fluoro-5-chloro-5H-dibenzo[a,d]cycloheptene and 1-(n-butyl)-4-piperidylmagnesium chloride.

4-(5H-Dibenzo[a,d]cyclohepten-5-yl)-1-(3-methylbutyl)piperidine from 5-chloro-5H-dibenzo[a,d]cycloheptene and 1-(3-methylbutyl-4-piperidyl)magnesium chloride.

4-(3-t-Butoxy-5H-dibenzo[a,d]cyclohepten-5-yl)-1-(t-butyl)piperidine from 3-(t-butoxy)-5-chloro-5H-dibenzo[a,d]cycloheptene and 1-(t-butyl)-4-piperidylmagnesium chloride.

4-(3-Chloro-5H-dibenzo[a,d]cyclohepten-5-yl)-1-(n-hexyl)piperidine from 3,5-dichloro-5H-dibenzo[a,d]cycloheptene and 1-(n-hexyl)-4-piperidylmagnesium chloride.

4-(5H-Dibenzo[a,d]cyclohepten-5-yl)-1-ethylpiperidine from 5-chloro-5H-dibenzo[a,d]cycloheptene and 1-ethyl-4-piperidylmagnesium chloride.

4-(3-Trigluoromethyl-5H-dibenzo[a,d]cyclohepten-5-yl)-1-methylpiperidine from 3-trifluoromethyl-5H-dibenzo[a,d]cycloheptene and 1-methyl-4-piperidylmagnesium chloride.

1-Ethyl-4-(3-trifluoromethyl-5H-dibenzo[a,d]cyclohepten-5-yl)piperidine from 4-(3-trifluormethyl)-5-chloro-5H-dibenzo[a,d]-cycloheptene and 1-ethyl-4-piperidylmagnesium chloride.

EXAMPLE XI

In operations carried out in a manner similar to that described in Example I, an appropriate 5-chloro-10,11-dihydro-5H-dibenzo[a,d]cycloheptene compound is first prepared by the reaction of thionyl chloride on an appropriate 10,11-dihydro-5H-dibenzo[a,d]cyclohepten-5-ol, and the 5-chloro intermediate reacted with the appropriate 4-piperidyl Grignard reagent.

In such operations, the following compounds may be prepared:

4-(3-Fluoro-10,11-dihydro-5H-dibenzo[a,d]cyclohepten-5-yl)-1-methylpiperidine from 4-(5-chloro-3-fluoro-10,11-dihydro-5H-dibenzo[a,d]cycloheptene and 1-methyl-4-piperidylmagnesium chloride.

4-(3-Chloro-10,11-dihydro-5H-dibenzo[a,d]cyclohepten-5-yl)-1-(3-methylbutyl)lpiperidine from 3,5-dichloro-10,11-dihydro-5H-dibenzo[a,d]cycloheptene and 1-(3-methybutyl)-4-piperidylmagnesium chloride.

4-(2-Bromo-10,11-dihydro-5H-dibenzo[a,d]cyclohepten-5-yl)-1-methylpiperidine from 2-bromo-5-chloro-10,11-dihydro-5H-dibenzo[a,d]cycloheptene and 1-methyl-4-piperidylmagnesium chloride.

4-(3-Methoxy-10,11-dihydro-5H-dibenzo[a,d]cyclohepten-5-yl)-1-isopropylpiperidine from 5-chloro 3-methoxy-10,11-dihydro-5H-dibenzo[a,d]cycloheptene and 1-isopropyl-4-piperidylmagnesium chloride.

4-(3-Trifluoromethyl-10,11-dihydro-5H-dibenzo[a,d]cyclohepten-5-yl)-1-isopropylpiperidine from 3-trifluoromethyl-5-chloro-10,11-dihydro-5H-dibenzo[a,d]cycloheptene and 1-methyl-4-piperidylmagnesium chloride.

EXAMPLE XII 4-(5H-Dibenzo[a,d]cyclohepten-5-yl)-1-methylpiperidine-1-oxide monohydrate

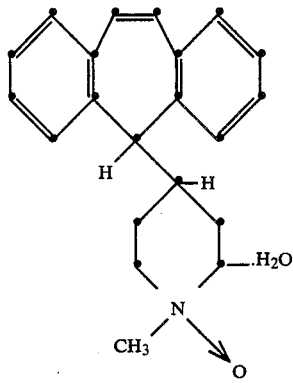

235 milligrams (6.9 millimoles) of 30 percent hydrogen peroxide was added in a single portion to a stirred solution of 2.0 grams (6.9 millimoles) of 4-(5H-dibenzo[a,d]cyclohepten-5-yl)-1-methylpiperidine in 40 milliliters of methanol. Subsequently, at two thirty-minute intervals, two additional 235 milligram portions of the 30 percent hydrogen peroxide were added. The mixture was stirred at room temperature and the progress of the reaction monitored by TLC (ammonia saturated chloroform). After stirring overnight, another 710 milligrams of 30 percent hydrogen peroxide was added in one portion and the reaction again allowed to proceed overnight. Thereafter, three more equivalents of hydrogen peroxide were added and the stirring continued for two days whereupon TLC analysis (20 percent methanol/80 percent chloroform) indicated substantial completion of the reaction with the formation of a 4-(5H-dibenzo[a,d]cyclohepten-5-yl)-1-methylpiperidine-1-oxide product in the reaction mixture. The unreacted hydrogen peroxide was decomposed by stirring with a 5 percent platinum on carbon suspension at room temperature for about 17 hours. The mixture was filtered through celite and the filtrate concentrated on a rotary evaporator ($t \leq 30°$ C.) to obtain a solid residue. The residue was crystallized by placing in boiling ethyl acetate and adding just enough acetonitrile to effect dissolution of the solid and the solution allowed to cool to obtain the product as white needles. The product after washing and drying, melted 215° to 222° C. after first turning brown at 205° C. Elemental analyses indicated the product to be a hydrate.

Calcd for $C_{21}H_{23}NO \cdot H_2O$: C, 77.98; H, 8.25; N, 4.33. Found: C, 78.32; H, 7.98; N, 4.23.

EXAMPLE XIII

The following salts may be prepared by mixing together the appropriate piperidine compound and appropriate acid:

4-(5H-Dibenzo[a,b]cyclohepten-5-yl)-1-methylpiperidine hydrogen maleate.

4-(3-Bromo-5H-dibenzo[a,d]cyclohepten-5-yl)-1-methylpiperidine hydrogen sulfate.

4-(5H-Dibenzo[a,d]cyclohepten-5-yl)-1-methylpiperidine hydrogen succinate.

4-(3-Methoxy-5H-dibenzo[a,d]cyclohepten-5-yl)-1-methylpiperidine hydrochloride.

4-(3-Chloro-5H-dibenzo[a,d]cyclohepten5-yl)-1-ethylpiperidine hydrogen phosphate.

4-(3-Isopropoxy-5H-dibenzo[a,d]cyclohepten-5-yl)-1-(n-propyl)piperidine hydrogen tartrate.

1-Ethyl-4-(3-trifluoromethyl-5H-dibenzo[a,d]cyclohepten-5-yl)piperidine hydrochloride.

EXAMPLE XIV

In operations carried out in a manner similar to that described in Example I for preparation of the piperidine compound and Example XII for the oxide, the following compounds may be prepared by the reaction of the corresponding piperidine compound and hydrogen peroxide:

4-(5H-Dibenzo[a,d]cyclohepten-5-yl)-1-cyclohexylpiperidine-1-oxide.

4-(3-Methoxy-5H-dibenzo[a,d]cyclohepten-5-yl)-1-(n-propyl)piperidine-1-oxide.

4-(5H-Dibenzo[a,d]cyclohepten-5-yl)-1-ethylpiperidine-1-oxide.

4-(3-Chloro-5H-dibenzo[a,d]cyclohepten-5-yl)-1-methylpiperidine-1-oxide.

4-(3-Bromo-5H-dibenzo[a,d]cyclohepten-5-yl)-1-methylpiperidine-1oxide.

4-(3-Methoxy-5H-dibenzo[a,d]cyclohepten-5-yl)-1-methylpiperidine-1-oxide.

1-Ethyl-4-(3-trifluoromethyl-5H-dibenzo[a,d]cyclohepten-5-yl)piperidine-1-oxide.

EXAMPLE XV 4-(5H-Dibenzo[a,d]cyclohepten-5-yl)-1-methylpiperidine, equatorial isomer A Grignard solution prepared from 13.4 grams (0.1 mole) of 1-methyl-4-chloropiperidine, 2.43 grams (0.1 gram atom) of magnesium and 100 milliliters of tetrahydrofuran is added dropwise with stirring to a cooled solution of 17.0 grams (0.075 mole) of 5-chloro-5H- dibenzo[a,d]cycloheptene in 100 milliliters of tetrahydrofuran. After completion of the addition, stirring is continued for several hours at ambient temperature. The solvent is then vaporized under reduced pressure to obtain a residue which is dissolved in a biphasic mixture of benzene and water. The benzene solution is washed, dried filtered and the solvent vaporized as previously described to obtain the desired 4-(5H-dibenzo[a,d]cyclohepten-5-yl)-1-methylpiperidine, equational isomer as residue.

EXAMPLE XVI

Isomerization of the Axial to the Equatorial Isomer

Isomerization of the 5H axial isomer of 4-(5H-dibenzo[a,d]cyclohepten-5-yl)-1-methylpiperidine to the 5H equatorial isomer was carried out in an NMR tube. 3.67 milligrams of the axial isomer was dissolved in 1 milliliter of CDCl$_3$ at 24° C. and the sample inserted into the probe of a Nicolet NT-360 NMR spectrometer where it was heated at 55° C.±1° C. NMR spectra ($^1$H) were obtained every 864 seconds until isomerization to the equatorial isomer was complete as evidenced by the disappearance of the singlet corresponding to the 5H-axial proton and appearance of the 5H-equatorial proton (about 48,727 seconds).

Examples XVII–XVII illustrate compositions suitable for carrying out the methods of the present invention.

EXAMPLE XVII 10,000 hard gelatin capsules each containing as the active ingredient 25 milligrams of (±)-4-(3-methoxy-5H-dibenzo[a,d]cyclohepten-5-yl)-1-methylpiperidine are prepared from the following formulation:

|  | Grams |
| --- | --- |
| Active ingredient | 250 |
| Lactose | 750 |
| Starch | 250 |
| Talc | 250 |
| Calcium stearate | 10 |

A uniform mixture of the active and supplementary ingredients is prepared and filled into two-piece hard gelatin capsules. The capsules are suitable for oral administration to provide therapeutic relief for patients with cardiovascular disorders by alleviating cardiac arrhythmias and/or peripheral vasoconstriction.

EXAMPLE XVIII

Capsules are made by substituting for 4-(3-methoxy-5H-dibenzo[a,d]cyclohepten-5-yl)-1-methylpiperidine in the formulation of Example XVII one of the following:
(1) 5H-Equatorial 4-(5H-dibenzo[a,d]cyclohepten-5-yl)-1-methylpiperidine;
(2) 5H-Equatorial (±)-4-(3-bromo-5H-dibenzo[a,d]cyclohepten-5-yl)-1-methylpiperidine
(3) 5H-Equatorial (−)-4-(3-bromo-5H-dibenzo[a,d]cyclohepten-5-yl)-1-methylpiperidine
(4) 5H-Axial (±)-4-(3-bromo-5H-dibenzo[a,d]cyclohepten-5-yl)-1-methylpiperidine.

EXAMPLE XIX 5000 compressed tablets, each containing as active ingredient 10 milligrams of 4-(5H-dibenzo[a,d]cyclohepten-5-yl)-1-methylpiperidine are prepared from the following formulation :

|  | Grams |
| --- | --- |
| Active ingredient | 50 |
| Starch | 70 |
| Dibasic calcium phosphate hydrous | 500 |
| Calcium stearate | 2.5 |

The ingredients are finely powdered, mixed well, and then granulated with 10 percent starch paste. The granulation is dried and compressed into tablets using starch as a disintegrant and calcium stearate as lubricant.

EXAMPLE XX

One liter of a parenteral suspension comprising 5 milligrams of 4-(3-bromo-5H-dibenzo[a,d]cyclohepten-5-yl)-1-methylpiperidine as active ingredient per milliliter is prepared from the following formulation:

|  | Grams |
| --- | --- |
| Active ingredient | 5.0 |
| Polysorbate 80 | 2.0 |
| Sodium chloride | 9.0 |
| Sodium carboxymethyl cellulose | 10.0 |
| Methyl paraben | 1.8 |
| Propyl paraben | 0.2 |
| Water for injection, U.S.P. q.s. to 1 liter |  |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

EXAMPLE XXI

Five liters of an oral suspension comprising 25 milligrams of 4-(5H-dibenzo[a,d]cyclohepten-5-yl)-1-methylpiperidine per 5 milliliters (teaspoonful) are prepared from the following formulation:

|  | Grams |
| --- | --- |
| Active ingredient | 25.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene glycol | 52.0 |
| FD&C Yellow β5 | 0.1 |
| Sodium cyclamate | 50.0 |
| Sodium saccharin | 5.0 |
| Orange flavor | 7.5 |
| Filtered purified water, q.s. to 5 liters |  |

The parabens are dissolved in propylene glycol and this solution is added to a solution containing sodium cyclamate, sodium saccharin and sucrose in half the volume of water. The bentonite is then suspended in hot (about 85° C.) water and stirred for 60 minutes and the resulting suspension added to the first solution.

The sulfosuccinate is then dissolved in some water and the active ingredient suspended therein. The antifoam emulsion is diluted to somewhat viscous but pourable (lotionlike) consistency and then is added to the suspension and mixed.

The suspension containing active ingredient is then added to the first mixture and stirred, then color and flavoring added, the resulting mixture diluted to volume with water and stirred to a homogeneous mixture. The mixture is then passed through a colloidal mill and used to fill suitable containers.

EXAMPLE XXII

Gelatin capsules are prepared in separate operations carried out in a manner similar to that described in Example XVII but substituting for the active ingredient other compounds having the formula represented by Formula I as follows:

(1) 4-(5H-dibenzo[a,d]cyclohepten-5-yl)-1-methylpiperidine-1-oxide monohydrate;
(2) 4-(3-bromo-10,11-dihydro-5H-dibenzo[a,d]cyclohepten-5-yl)-1-isopropylpiperidine;
(3) 4-(10,11-dihydro-5H-dibenzo[a,d]cyclohepten-5-yl)piperidine;
(4) 4-(3-methoxy-5H-dibenzo[a,d]cyclohepten-5-yl)-1-(n-propyl)piperidine-1-oxide;
(5) 4-(3-chloro-5H-dibenzo[a,d]cyclohepten-5-yl)-1-methylpiperidine-1-oxide.
(6) 4-(3-methoxy-10,11-dihydro-5H-dibenzo[a,d]cyclohepten-5-yl)-1-isopropylpiperidine.

What is claimed is:
1. A method for treating cardiovascular disorders caused by high cellular concentration of $Ca^{++}$ comprising administering to a patient in need of such treatment a therapeutically effective amount for treatment of cardiovascular disorders caused by high cellular concentrations of $Ca^{++}$ of a compound having the formula:

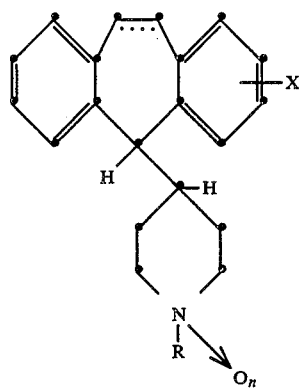

wherein the $\cdots$ bond denotes a saturated single bond or an unsaturated double bond, X is hydrogen, halogen, trifluoromethyl or lower alkoxy and R is hydrogen, lower alkyl containing from 1 to 6 carbon atoms or cycloalkyl containing from 3 to 6 carbon atoms and n is 0 or 1, or a pharmaceutically acceptable acid addition salt thereof.

* * * * *